United States Patent
Anderson et al.

(10) Patent No.: US 10,317,896 B2
(45) Date of Patent: Jun. 11, 2019

(54) METHODS AND APPARATUS TO USE VIBRATION DATA TO DETERMINE A CONDITION OF A PROCESS CONTROL DEVICE

(71) Applicant: Fisher Controls International LLC, Mashalltown, IA (US)

(72) Inventors: Shawn William Anderson, Haverhill, IA (US); Roger Anders, Mashalltown, IA (US); Ted Dennis Grabau, Mashalltown, IA (US)

(73) Assignee: FISHER CONTROLS INTERNATIONAL LLC, Marshalltown, IA (US)

( * ) Notice: Subject to any disclaimer, the term of this patent is extended or adjusted under 35 U.S.C. 154(b) by 257 days.

(21) Appl. No.: 15/354,058

(22) Filed: Nov. 17, 2016

(65) Prior Publication Data

US 2017/0068241 A1    Mar. 9, 2017

Related U.S. Application Data

(63) Continuation of application No. 13/534,681, filed on Jun. 27, 2012, now Pat. No. 9,528,629.

(51) Int. Cl.
*F16K 37/00* (2006.01)
*G01N 29/38* (2006.01)
(Continued)

(52) U.S. Cl.
CPC ...... *G05B 23/0235* (2013.01); *F16K 37/0083* (2013.01); *G01N 29/38* (2013.01);
(Continued)

(58) Field of Classification Search
CPC ...... G05B 23/0235; G05B 2219/33326; G05B 2219/37351; G05B 2219/37432;
(Continued)

(56) References Cited

U.S. PATENT DOCUMENTS 4,831,365 A    5/1989 Thomas et al.
5,115,672 A    5/1992 McShane et al.
(Continued)

FOREIGN PATENT DOCUMENTS

| CN | 1722036 | 1/2006 |
|---|---|---|
| EP | 0489597 | 6/1992 |
| WO | 0101213 | 1/2001 |

OTHER PUBLICATIONS

Shane Butler, "Prognostic Algorithms for Condition Monitoring and Remaining Useful Life Estimation," Sep. 2012, National University of Ireland Maynooth, 271 pages.
(Continued)

*Primary Examiner* — Justin Seo
*Assistant Examiner* — John M Royston
(74) *Attorney, Agent, or Firm* — Hanley, Flight & Zimmerman, LLC

(57) ABSTRACT

Methods and apparatus to use vibration data to determine a condition of a process control device are disclosed. An example apparatus includes a vibration monitoring circuit to: collect first vibration data associated with a process control device during calibration of the process control device; calculate an operating threshold of the process control device based on the first vibration data; collect usage information associated with the process control device, the usage information indicative of a remaining portion of useful life associated with the process control device; adjust the operating threshold based on the usage information, the adjusted operating threshold reflective of the remaining portion of useful life associated with the process control device; and determine a condition of the process control device if second vibration data associated with the process control device collected after the calibration exceeds the adjusted operating threshold.

20 Claims, 7 Drawing Sheets

(51) Int. Cl.
*G01N 29/44* (2006.01)
*G05B 23/02* (2006.01)

(52) U.S. Cl.
CPC ............... *G01N 29/4427* (2013.01); *G05B 2219/33326* (2013.01); *G05B 2219/37351* (2013.01); *G05B 2219/37432* (2013.01); *G05B 2219/37534* (2013.01); *G05B 2219/45006* (2013.01)

(58) Field of Classification Search
CPC .......... G05B 2219/37534; G05B 2219/45006; G01N 29/4427; F16K 37/0083
See application file for complete search history.

(56) References Cited

U.S. PATENT DOCUMENTS

| | | | |
|---|---|---|---|
| 5,319,296 A | 6/1994 | Patel | |
| 5,549,137 A | 8/1996 | Lenz et al. | |
| 6,601,005 B1 | 7/2003 | Eryurek et al. | |
| 7,484,416 B1 * | 2/2009 | Klosinski | G01L 9/0072 714/25 |
| 7,627,441 B2 | 12/2009 | Longsdorf et al. | |
| 2003/0130811 A1 * | 7/2003 | Boerhout | G01H 1/003 702/56 |
| 2005/0072239 A1 | 4/2005 | Longsdort et al. | |
| 2005/0118703 A1 | 6/2005 | Su | |
| 2006/0136110 A1 | 6/2006 | Casey et al. | |
| 2006/0265106 A1 | 11/2006 | Giles et al. | |
| 2007/0229248 A1 | 10/2007 | Mott et al. | |
| 2008/0243287 A1 | 10/2008 | Potdar et al. | |

OTHER PUBLICATIONS

United States Patent and Trademark Office, "Final Office Action," issued in connection with U.S. Appl. No. 13/534,681, dated Apr. 14, 2016, 37 pages.

United States Patent and Trademark Office, "Non-Final Office Action," issued in connection with U.S. Appl. No. 13/534,681, dated Aug. 27, 2015, 34 pages.

United States Patent and Trademark Office, "Notice of Allowance and Fee(s) Due," issued in connection with U.S. Appl. No. 13/534,681, dated Aug. 16, 2016, 21 pages.

International Searching Authority, "International Search Report," issued in connection with PCT Application No. PCT/US2013/047758, dated Sep. 27, 2013, 3 pages.

International Searching Authority, "International Preliminary Report on Patentability," issued in connection with PCT Application No. PCT/US2013/047758, dated Dec. 31, 2014, 12 pages.

State Intellectual Property Office of China, "First Office Action," issued in connection with Chinese Patent Application No. 201310262785.5, dated Sep. 2, 2016, 38 pages.

* cited by examiner

METHODS AND APPARATUS TO USE VIBRATION DATA TO DETERMINE A CONDITION OF A PROCESS CONTROL DEVICE

RELATED APPLICATION

This patent arises from a continuation of U.S. application Ser. No. 13/534,681, which was filed on Jun. 27, 2012, and is hereby incorporated herein by reference in its entirety.

FIELD OF THE DISCLOSURE

This disclosure relates generally to process control devices and, more particularly, to methods and apparatus to use vibration data to determine a condition of a process control device.

BACKGROUND

Process control systems generally use a variety of process control devices to control a process. Vibrations in components in these process control devices are inherent during operation. Over time, components included in these process control devices are subject to stresses that cause changes in vibration patterns associated with the components. These stresses may decrease performance of the process control devices and reduce the remaining useful life of the components and, thus, the process control devices. As these stresses can impact a process control device to varying degrees, the useful life of a process control device also varies.

SUMMARY

An example apparatus includes a vibration monitoring circuit. The vibration monitoring circuit is to: collect first vibration data associated with a process control device during calibration of the process control device; calculate an operating threshold of the process control device based on the first vibration data; collect usage information associated with the process control device, the usage information indicative of a remaining portion of useful life associated with the process control device; adjust the operating threshold based on the usage information, the adjusted operating threshold reflective of the remaining portion of useful life associated with the process control device; and determine a condition of the process control device if second vibration data associated with the process control device collected after the calibration exceeds the adjusted operating threshold.

Another example apparatus includes a vibration monitoring circuit. The vibration monitoring circuit is to: collect first vibration data from a process control device and second vibration data from a pipe coupled to the process control device; calculate a ratio based on the first vibration data and the second vibration data; collect usage information associated with the process control device, the usage information indicative of a remaining portion of useful life associated with the process control device; adjust a threshold value based on the usage information, the adjusted threshold value reflective of the remaining portion of useful life associated with the process control device; and determine a condition of the process control device if the ratio is greater than the adjusted threshold value.

Another example apparatus includes a vibration monitoring circuit. The vibration monitoring circuit is to: collect vibration data from a process control device; access a predetermined diagnostic vibration pattern associated with the process control device; collect usage information associated with the process control device, the usage information indicative of a remaining portion of useful life associated with the process control device; adjust the predetermined diagnostic vibration pattern based on the usage information, the adjusted diagnostic vibration pattern reflective of the remaining portion of useful life associated with the process control device; compare the vibration data to the adjusted diagnostic vibration pattern; and determine a condition of the process control device based on the comparison.

Another example apparatus includes a vibration monitoring circuit. The vibration monitoring circuit is to: collect usage information associated with a process control device, the usage information indicative of a remaining portion of useful life associated with the process control device; adjust a known threshold range associated with the process control device based on the usage information, the adjusted known threshold range reflective of the remaining portion of useful life associated with the process control device; collect first vibration data from the process control device; identify a characteristic of the process control device from the first vibration data; determine if the characteristic is within the adjusted known threshold range; and if the characteristic is within the adjusted known threshold range, determine a condition of the process control device.

DETAILED DESCRIPTION

Figure 1:
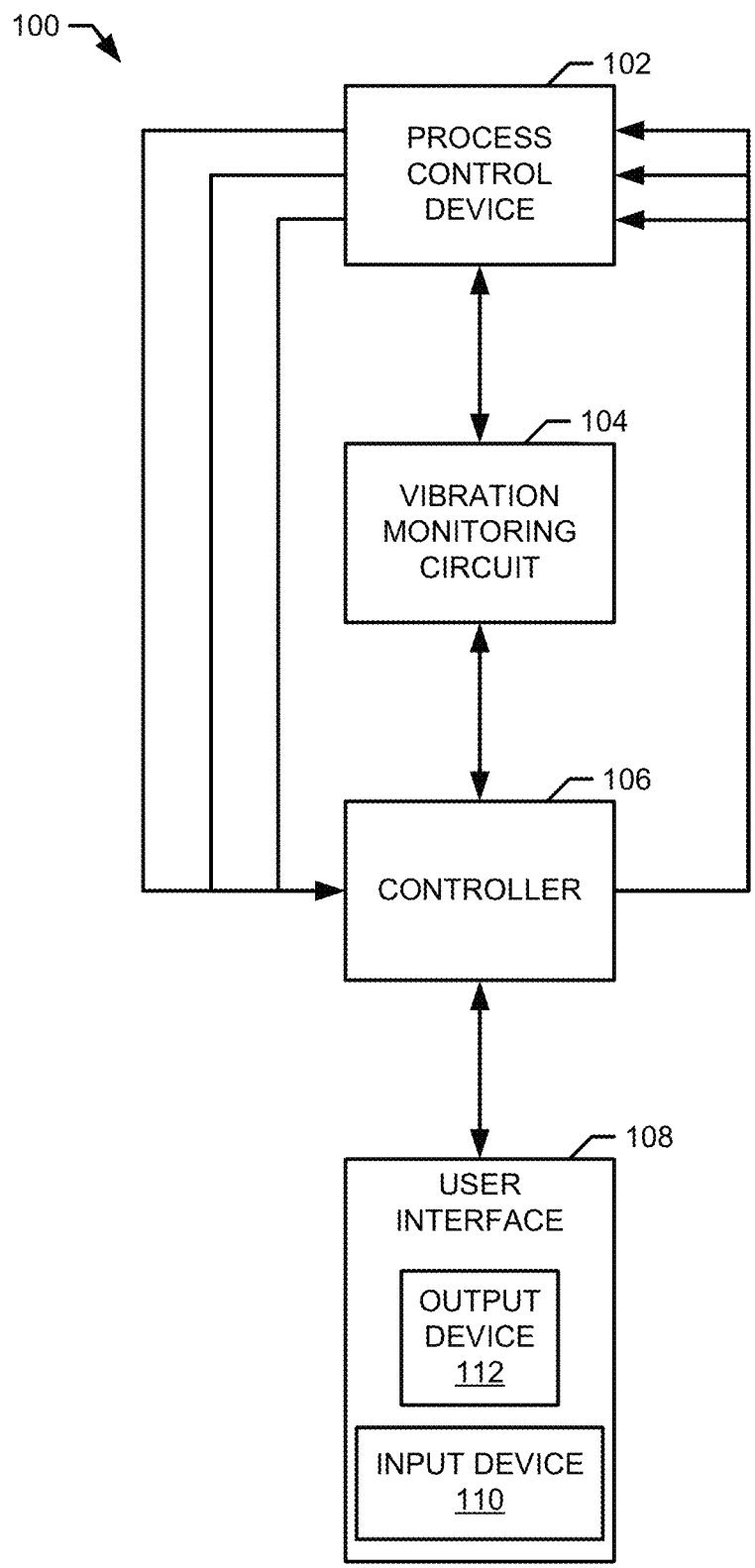
FIG. 1 illustrates an example process control system within which the teachings of this disclosure may be implemented.

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

While the following methods and apparatus are described in conjunction with a control valve assembly, the example methods and apparatus may also be used with any other process control device. Processes such as, for example, industrial processes are usually controlled by a variety of process control devices. These process control devices may include actuators and linear valves. Over time, structural damage or wear to one or more of the process control devices may develop and lead to conditions such as, for example, control instability and/or other performance degradation of the process control devices.

The examples described herein relate to processing vibration data collected from a process control device and determining a condition of the process control device based on the vibration data. Vibration data may have characteristics relating to frequency, acceleration, displacement and/or velocity associated with components of the process control device and can provide information regarding the structural or functional integrity of the process control device. Vibration data nearing a threshold or a shift identified in the vibration data may indicate the onset of a failure for which an alert may be provided to a user or other person. For example, vibration data can indicate control instability due to control system tuning, valve controller tuning, and/or other process issues relating to the process control device.

In some examples, vibration data collected from one or more vibration sensors operatively coupled to a process control device can be processed to identify a threshold associated with a condition of the process control device. For example, vibration data collected from a sensor, such as an accelerometer, operatively coupled to a component of the process control device can be collected during calibration and used to calculate an operating threshold of the process control device. Alternatively, the operating threshold may be a known threshold such as, for example, an industry standard or accepted limit or threshold. Vibration data collected from the sensor after calibration can be compared to the operating threshold and a condition of the process control device may be determined if the operating threshold is exceeded.

In other examples, vibration data is collected from an additional sensor operatively coupled to a pipe, which is coupled to the process control device. In such examples, vibration data collected from a sensor operatively coupled to the process control device and vibration data collected from the sensor operatively coupled to the pipe may be used to calculate a ratio. This ratio may be compared to a threshold value and a condition of the process control device may be determined when the ratio exceeds the threshold value. The value of the threshold may depend on the location of the sensor operatively coupled to the process control device.

In other examples, diagnostic vibration data may be used to determine a condition of the process control device. Diagnostic vibration data may include an operating threshold, a predetermined threshold, a threshold value and/or a range. When the diagnostic vibration data includes a frequency range, a determination of the condition of the process control device may be made based on a comparison of the collected vibration data from a sensor operatively coupled to the process control device to the diagnostic vibration data.

FIG. 1 illustrates an example process control system 100 that may be used to implement the example methods and apparatus disclosed herein. In the illustrated example of FIG. 1, a process control device 102, a vibration monitoring circuit 104, a controller 106 and a user interface 108 may communicate via, for example, wired or wireless links. In particular, the example process control device 102 and the example controller 106 of FIG. 1 may communicate via a data bus (e.g., FOUNDATION Fieldbus™, HART™, Profibus™, Modbus™, Devicenet™, etc.) or a Local Area Network (LAN).

The vibration monitoring circuit 104 of FIG. 1 collects the vibration data communicated by the process control device 102 and generates alert messages to output to the controller 106. The example vibration monitoring circuit 104 of FIG. 1 and/or the example controller 106 of FIG. 1 may be a digital valve positioner (DVP), a processor for data collection and/or discrimination, and/or an asset management software package. Alternatively, the example vibration monitoring circuit 104 of FIG. 1 and the controller 106 may be combined and/or integrated into, for example, a DeltaV™ controller.

The example controller 106 generates notifications, alert messages, and/or other information based on information received and/or collected from the process control device 102 and/or the vibration monitoring circuit 104. The example controller 106 of FIG. 1 also transmits information (e.g., instructions) to the process control device 102 and/or outputs information (e.g., alert messages) to the user interface 108.

The example process control device 102 of FIG. 1 may be any number of input devices and/or output devices. In some examples, the input devices include valves, pumps, fans, heaters, coolers, mixers, and/or other devices, and the output devices include accelerometers, thermometers, pressure gauges, concentration gauges, fluid level meters, flow meters, vapor sensors, valve positioners, and/or other devices.

The example user interface 108 of FIG. 1 is any device that processes inputs and outputs such as, for example, a computer, a workstation, a server, and/or a mobile device, etc. User input may be communicated to the user interface 108 by the input device 110 such as, for example, a keyboard, a stylus pen, a mouse, and/or a touch screen, etc. Output from the user interface 108 may be communicated to the user by the output device 112 such as, for example, a monitor (e.g., displaying an alert message) and/or speaker (e.g., emitting an audible alert), etc.

Although a single example vibration monitoring system 104 and example controller 106 are shown in FIG. 1, one or more additional example vibration monitoring circuits 104 and/or controllers 106 may be included in the example process control system 100 of FIG. 1 without departing from the teachings of this disclosure.

Figure 2:
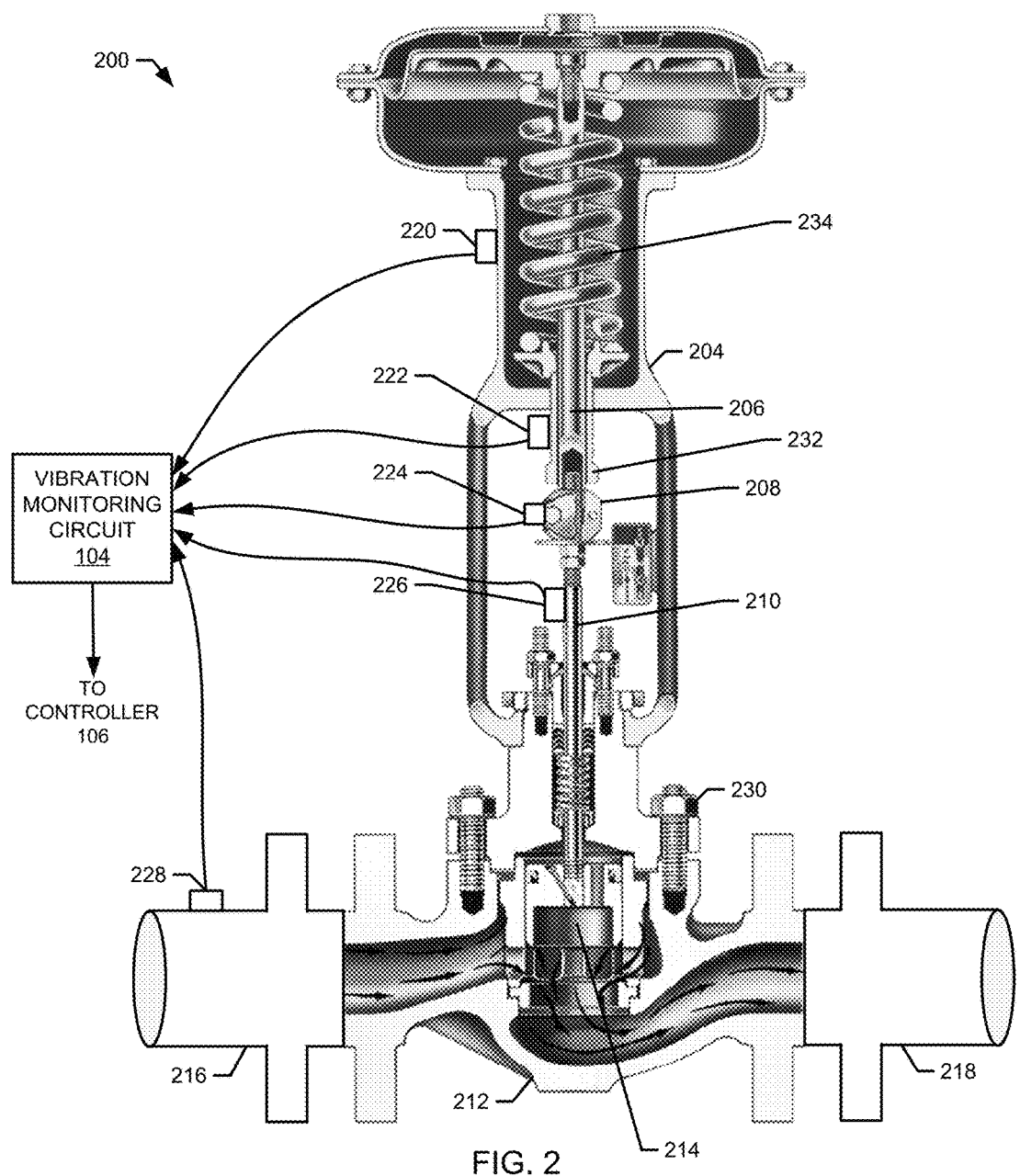
FIG. 2 illustrates an example process control device that may be used to implement example methods disclosed herein.

FIG. 2 illustrates an example process control device 200 that may be used to implement the example methods and apparatus disclosed herein. The example process control device 200 shown in FIG. 2 is a linear valve. However, other process control devices may also be used to implement the example methods and apparatus disclosed herein. The example process control device 200 includes an actuator 204, an actuator rod 206, a stem connector 208, a valve stem 210, a valve body 212, and a valve plug 214. The example valve body 212 of FIG. 2 may also be coupled to an upstream pipe 216 and a downstream pipe 218. First through fifth sensors 220, 222, 224, 226 and 228 are coupled to the example actuator 204, the example actuator rod 206, the example stem connector 208, the example valve stem 210 and the example upstream pipe 216, respectively. In the example of FIG. 2, the sensors 220-228 may include one or more accelerometers and/or other vibration or motion sensors. Although not shown, one or more sensors may also be coupled to the downstream pipe 218. Additionally, although the example process control device 200 includes the sensors 220-228, it is possible to use fewer sensors or additional sensors in the locations shown in FIG. 2 or in one or more different locations.

The mechanical connections between the components of the example process control device 200 may vibrate during operation of the process control device 200. These vibrations may be due to a variety of sources such as motor or actuator operation, fluid movement through the process control device 200, looseness of one or more mechanical connections, etc. In some examples, vibrations or vibration patterns may indicate a particular condition of the process control device 200. For example, vibration data retrieved from a sensor coupled to the actuator rod 206 (e.g., the actuator rod sensor 222), the stem connector 208 (e.g., the stem connector sensor 224) or the valve stem 210 (e.g., the valve stem sensor 226) may indicate looseness, wear or other degradation of the corresponding component.

In the illustrated example of FIG. 2, vibration data collected via one or more of the sensors 220-228 is communicated (e.g., via a wired or wireless link) to the example vibration monitoring circuit 104. For example, vibration data corresponding to the example actuator 204 is measured or gathered by the actuator housing sensor 220. This vibration data may be communicated from the actuator housing sensor 220 to the example vibration monitoring circuit 104 for further processing.

The vibration data received from the example sensors 220-228 may be used by the example vibration monitoring circuit 104 to indicate a condition of the process control device 200. The vibration monitoring circuit 104 determines the characteristics of the vibration data relating to frequency, acceleration, displacement and/or velocity collected from the sensor(s) 220-228 coupled to the corresponding component(s) of the process control device 200. In some examples, the vibration monitoring circuit 104 also identifies the source of the vibration data (e.g., the sensor from which the data is obtained). In some examples, the vibration monitoring circuit 104 identifies the axis of movement associated with the vibration data. For example, the vibration data received from a sensor may correspond to displacement of a component of the process control device 200 along a horizontal axis and/or a vertical axis.

The example vibration monitoring circuit 104 compares the identified characteristic(s) of the vibration data to a known threshold value(s) and/or range(s). For example, displacement, velocity and/or acceleration characteristic(s) of the vibration data may be compared to a known threshold value or multiple threshold values. When the vibration data exceeds the known threshold value(s), the example vibration monitoring circuit 104 may identify a condition of the process control device 200 such as a loose bonnet fastener 230. Additionally or alternatively, the frequency characteristics of the vibration data may be compared to a threshold value and/or to a range or multiple ranges. For example, a broken or damaged valve plug 214 may be identified by the example vibration monitoring circuit 104 when a fundamental frequency of vibration exceeds 100 Hertz (Hz). Additionally or alternatively, the example vibration monitoring circuit 104 may identify, for example, control instability in the example process control device 200 due to control system tuning or valve controller tuning when a fundamental frequency of vibration is between 1 Hz and 10 Hz.

The known threshold values and/or ranges used by the example vibration monitoring circuit 104 to compare to the vibration data may be stored in a local memory in the example vibration monitoring circuit 104 and/or retrieved from a remote storage via a wired or wireless link. The known threshold value(s) and/or range(s) may be based on information gathered during product testing in a laboratory or may be set by industry standards. For example, laboratory testing may identify vibration data characteristic(s) associated with a component of the process control device 200 corresponding to particular conditions of the process control device 200. Additionally or alternatively, the example vibration monitoring circuit 104 may calibrate during, for example, an initial setup period. During calibration, the example vibration monitoring circuit 104 may collect vibration data from the example sensors 220-228 over a period of time (e.g., ten minutes) and normalize the vibration data. This normalized vibration data may be stored (e.g., in a local memory) and may be compared to subsequently received vibration data by the vibration monitoring circuit 104 to identify a condition of the process control device 200.

In some examples, the vibration monitoring circuit 104 compares the vibration data received from, for example, the example stem connector sensor 224 to a threshold value corresponding to a condition relating to the stem connector 208. For example, when the vibration data collected from the stem connector sensor 224 (e.g., characteristics relating to frequency) exceeds a threshold value, the vibration monitoring circuit 104 may identify a condition associated with compromise of the structural and/or functional integrity of the process control device 200. For example, vibration data received from the stem connector sensor 224 greater than 100 Hz may indicate internal damage to the valve body 212 such as a broken valve plug 214 or piston ring in a piston actuator (not shown).

In some examples, the vibration monitoring circuit 104 compares the received vibration data to stored ranges corresponding to conditions relating to the process control device 200. For example, when the frequency (e.g., fundamental) of the vibration data received from, for example, the actuator rod sensor 222 is between 10 Hertz and 100 Hertz, the vibration monitoring circuit 104 may identify a condition associated with, for example, looseness of a component due to impaired guiding of the reciprocating parts due to a worn actuator guiding bushing 232.

In other examples, the vibration monitoring circuit 104 may calibrate prior to using vibration data collected from the sensors 220-228 to identify a condition of the process control device 200. For example, when the process control device 200 is installed in a process control system such as the example process control system 100 of FIG. 1, the vibration monitoring circuit 104 collects vibration data from a sensor (e.g., the example sensors 220-228) operatively coupled to a component of the process control device 200 over a period of time. For example, the vibration monitoring circuit 104 may collect vibration data from the example stem connector sensor 224 of FIG. 2 over a 24 hour period. The collected vibration data may then be normalized and a vibration pattern (e.g., natural frequency) of the example stem connector 208 during operation (e.g., an operating threshold and/or range) may be identified by the example vibration monitoring circuit 104. For example, the normal distribution of the received vibration data is calculated.

Once calibrated, the vibration monitoring circuit 104 monitors the vibration data received from the example stem connector sensor 224. When the vibration data received by the vibration monitoring circuit 104 deviates from the normalized vibration pattern determined during calibration (e.g., the operating threshold and/or range), the example vibration monitoring circuit 104 identifies a condition of the process control device 200 such as a loose stem connector 208.

In other examples, the vibration monitoring circuit 104 continuously (e.g., periodically, aperiodically) collects vibration data from the example stem connector sensor 224 and identifies a new vibration pattern of the stem connector 208. When the new vibration pattern differs from the normalized vibration pattern (e.g., the natural frequency of the stem connector 208 during operation), the example vibration monitoring circuit 104 may identify, for example, looseness in the moving components of the valve assembly due to wear or damage to a seal associated with the example valve plug 214.

In some examples, the vibration monitoring circuit 104 collects and processes vibration data from sensors coupled to multiple components of the process control device 200. For example, the vibration monitoring circuit 104 collects vibration data from the trim (e.g., an internal component in the process control device 200 such as the example actuator 204) and from the external body (e.g., the example pipe 216) via the example sensors 220 and 228, respectively. The example vibration monitoring circuit 104 may calculate a transmissibility ratio based on the vibration data collected via the example sensors 220 and 228. The transmissibility ratio is a ratio of the output amplitude to the input amplitude. Thus, in the illustrated example, this ratio represents an amplification of the movement from the pipe 216 to the actuator 204. For example, the transmissibility ratio may be calculated by the amount of displacement measured by the actuator sensor 220 divided by the amount of displacement measured by the piping sensor 228. This ratio may be compared to a threshold and, when the ratio exceeds the threshold, the vibration monitoring circuit 104 may identify an excessive amount of amplification as the center of gravity of the actuator 204 moves further from the pipe 216 centerline. Alternatively, the example vibration monitoring circuit 104 may calculate the difference between vibration data collected from the trim and the external body of the process control device 200. For example, the vibration monitoring circuit 104 may calculate the difference between frequencies collected from the example sensors 220 and 228. When this difference exceeds a threshold, the vibration monitoring circuit 104 may identity instable tuning (e.g., looseness in the guiding) due to a worn seal or excess vibration induced by the process flow.

In the illustrated example of FIG. 2, when the vibration monitoring circuit 104 identifies a condition of the process control device 200, the vibration monitoring circuit 104 outputs an indication to the example controller 106 of FIG. 1 and/or the example user interface 108 of FIG. 1. For example, when the vibration monitoring circuit 104 identifies structural damage in the process control device 200, the vibration monitoring circuit 104 outputs an indication to the example controller 106. In some examples, the vibration monitoring circuit 104 outputs an indication to the example controller 106 when an event occurs (e.g., a condition is identified). In some examples, the vibration monitoring circuit 104 continuously outputs (e.g., periodically, aperiodically) an indication relating to the condition of the process control device 200.

In some examples, a digital valve positioner (DVP) may also be coupled to the process control device 200 to collect information from the process control device. For example, the DVP may collect and determine information such as, for example, a position of the actuator rod 206 and/or the valve stem 210, a direction of travel, information received from sensors (e.g., vibration data), and/or other information. During operation, the DVP transmits the information to the controller 106 of FIG. 1 and receives information from the example controller 106.

Figure 3:
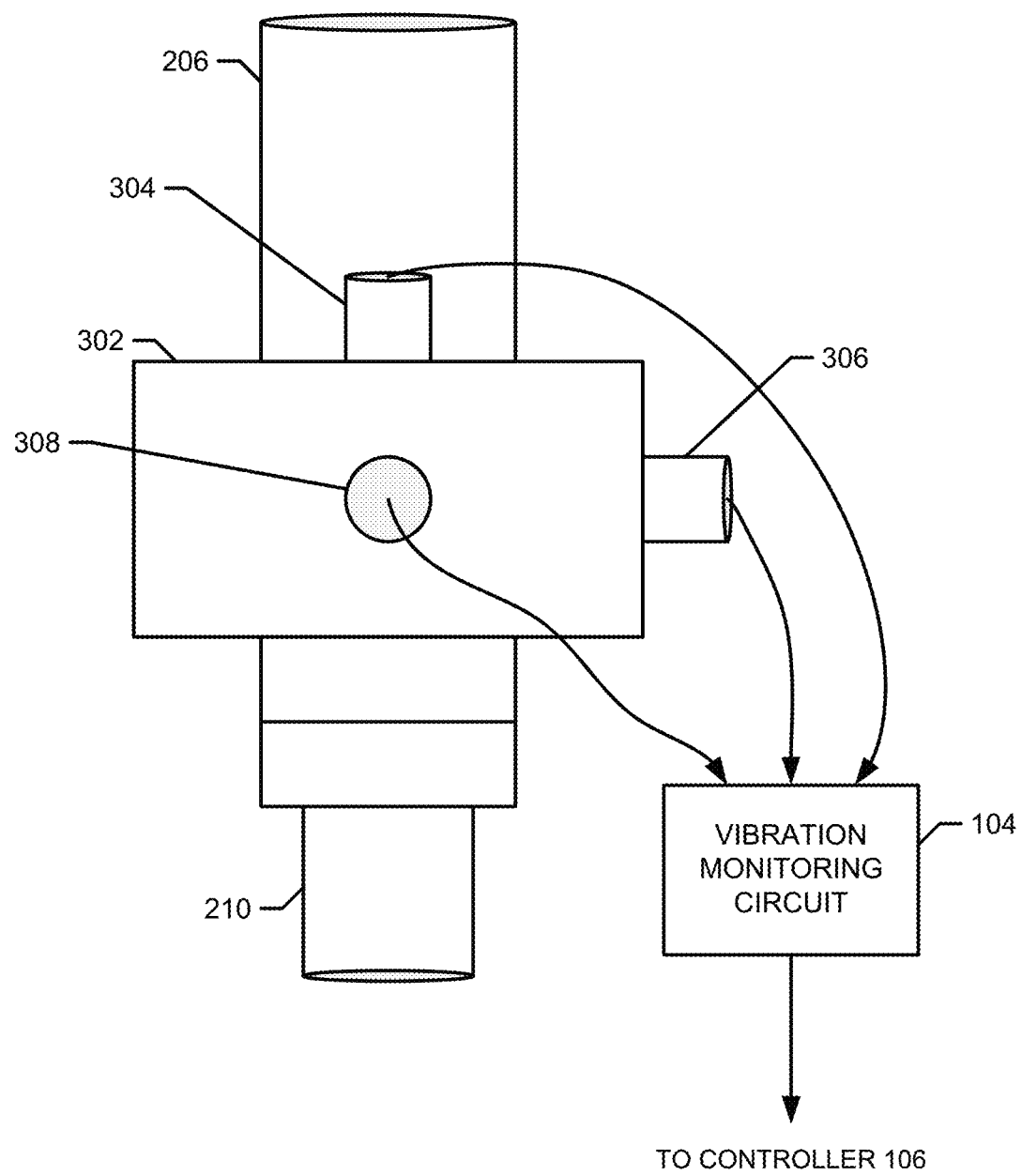
FIG. 3 illustrates an alternate example of the stem connector of FIG. 2.

FIG. 3 illustrates an alternate example stem connector 302 that may be used with the example process control device 200 of FIG. 2. The example stem connector 302 of FIG. 3 is coupled to the example actuator rod 206 and the example valve stem 210 described above in connection with FIG. 2. First through third sensors 304, 306 and 308 are operatively coupled to the example stem connector 208. Each of these sensors 304-308 measures vibration data from the stem connector 302 on a mutually perpendicular axis. For example, the first sensor 304 measures vibration data relating to the example stem connector 302 (e.g., displacement of the stem connector 302) along a first axis relative to the stem connector 302, the second sensor 306 measures vibration data relating to the example stem connector 302 (e.g., displacement of the stem connector 302) along a second axis relative to the stem connector 302, and the third sensor 308 measures vibration data relating to the example stem connector 302 (e.g., displacement of the stem connector 302) along a third axis relative to the stem connector 302.

In the illustrated example of FIG. 3, the example vibration monitoring circuit 104 collects vibration data from each sensor coupled to the example stem connector 302 (e.g., the sensors 304-308), processes the vibration data and compares the vibration data to a known threshold and/or range. For example, the vibration monitoring circuit 104 calculates a ratio based on the received vibration data from first and second sensors 304 and 306. In the illustrated example, when the calculated ratio exceeds a threshold associated with vibration data from the stem connector 302, the vibration monitoring circuit 104 identifies a condition of the process control device 200 of FIG. 2.

Figure 4:
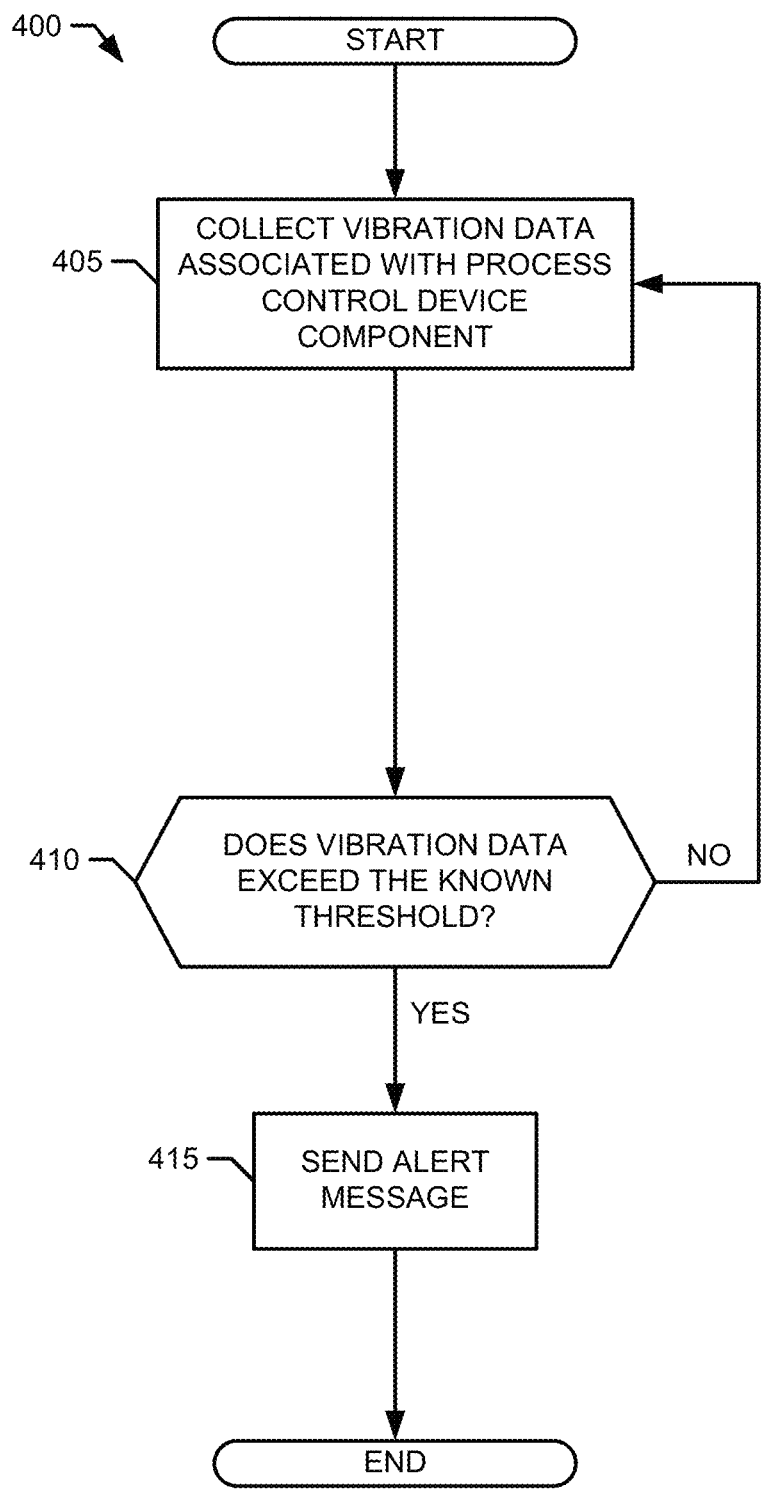
FIG. 4 is a flow chart representative of an example method disclosed herein.
Figure 5:
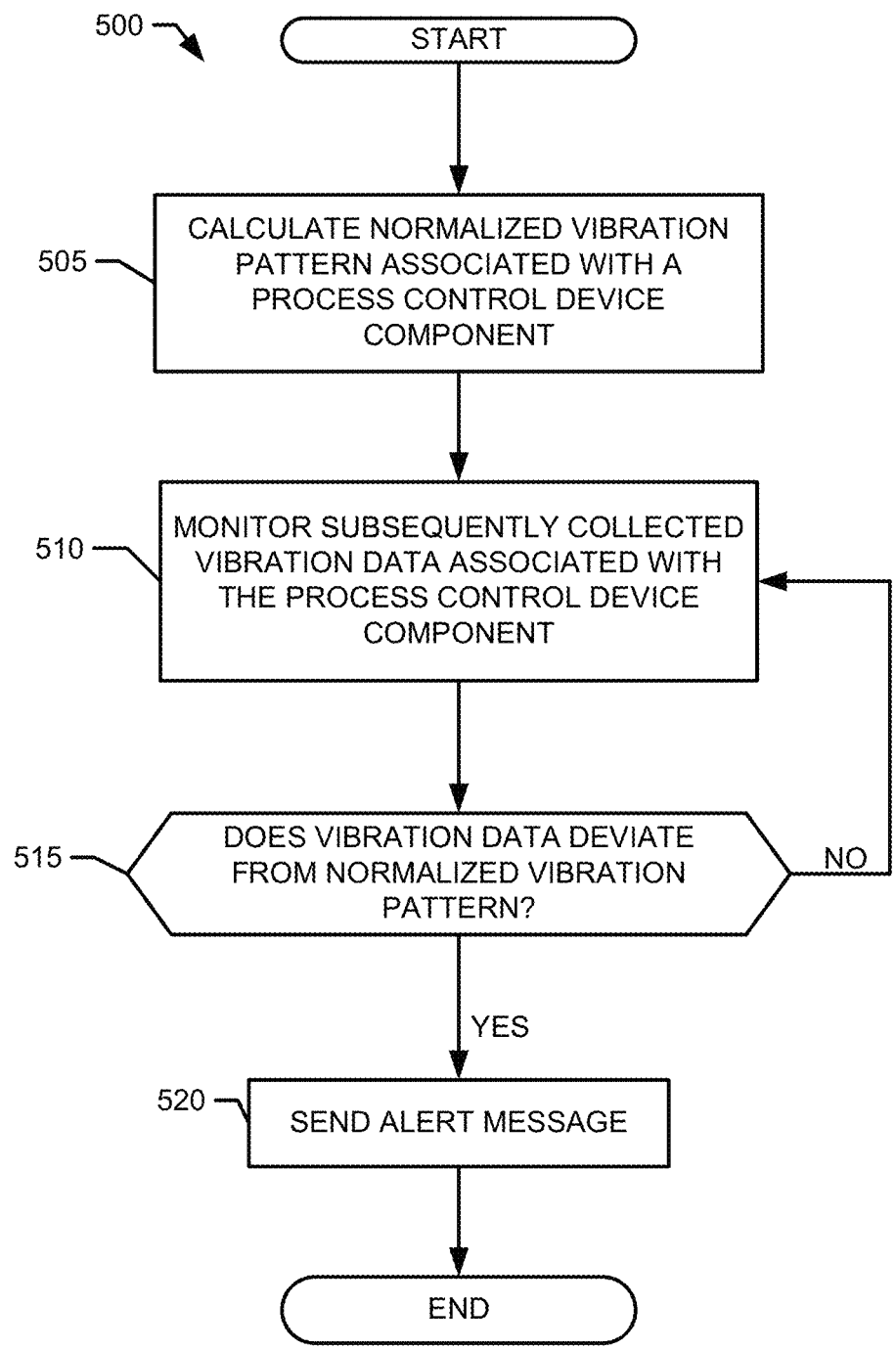
FIG. 5 is a flow chart representative of another example method disclosed herein.
Figure 6:
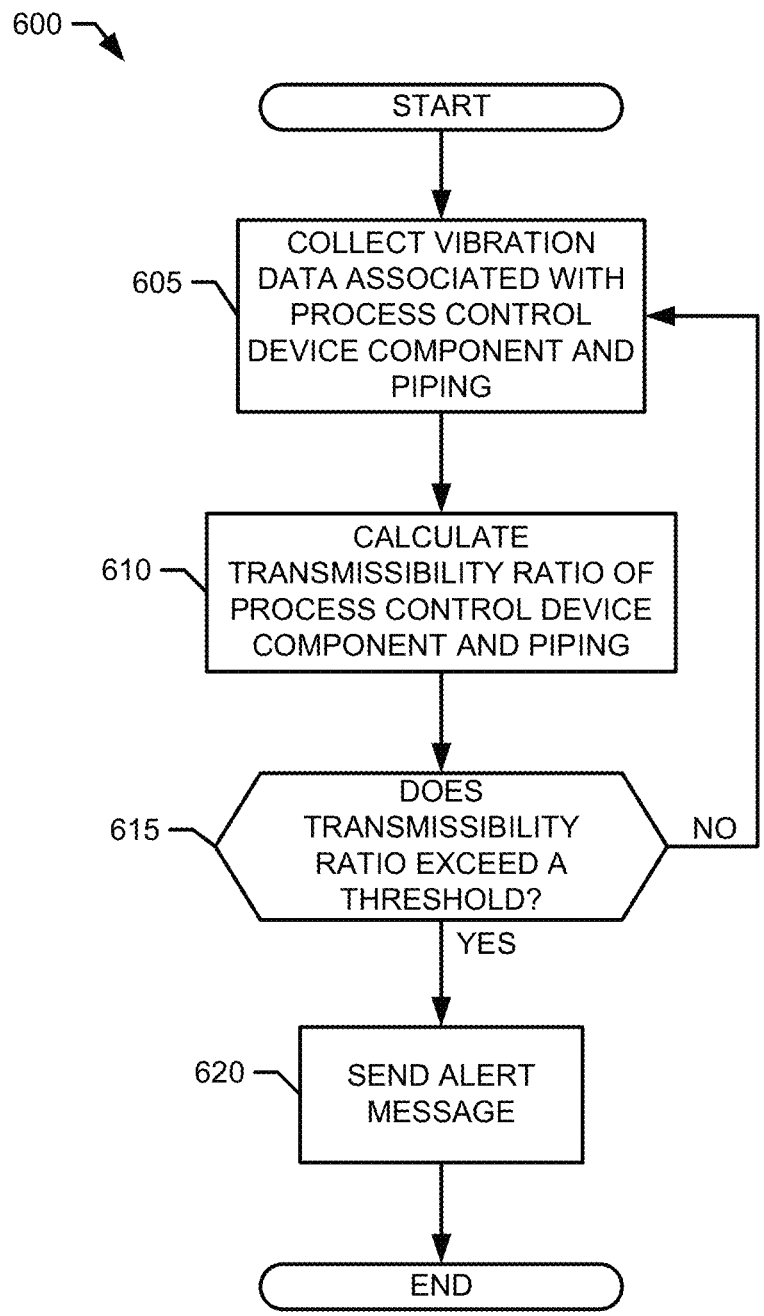
FIG. 6 is a flow chart representative of another example method disclosed herein.

FIGS. 4, 5 and 6 are flowcharts representative of example methods disclosed herein. Some or all of the example methods of FIGS. 4, 5 and 6 may be carried out by a processor, the controller 106 and/or any other suitable processing device. In some examples, some or all of the example methods of FIGS. 4, 5 and 6 are embodied in coded instructions stored on a tangible machine accessible or readable medium such as a flash memory, a ROM and/or random-access memory RAM associated with a processor. Alternatively, some or all of the example methods of FIGS. 4, 5 and 6 may be implemented using any combination(s) of application specific integrated circuit(s) (ASIC(s)), programmable logic devices(s) (PLD(s)), field programmable logic device(s) (FPLD(s)), discrete logic, hardware, firmware, etc. Also, one or more of the operations depicted in FIGS. 4, 5 and 6 may be implemented manually or as any combination of any of the foregoing techniques, for example, any combination of firmware, software, discrete logic and/or hardware. Further, although the example methods are described in reference to the flowcharts illustrated in FIGS. 4, 5 and 6, many other methods of implementing the example methods may be employed. For example, the order of execution of the blocks may be changed, and/or some of the blocks described may be changed, eliminated, subdivided, or combined. Additionally, any or all of the example methods of FIGS. 4, 5 and 6 may be carried out sequentially and/or carried out in parallel by, for example, separate processing threads, processors, devices, discrete logic, circuits, etc.

With reference to FIGS. 1-3, the example method or process 400 of FIG. 4 begins by collecting vibration data associated with a component of the process control device 200 (block 405). In some examples, the mechanical connections between the components of the process control device 200 may introduce vibrations during operation of the process control device 200. During operation, the sensor operatively coupled to a component of the process control device 200 (e.g., the example sensors 220-228 of FIG. 2) measures the vibrations corresponding to the component. This vibration data is communicated (e.g., via a wired or wireless link) to the example vibration monitoring circuit 104. The example vibration monitoring circuit 104 continuously (e.g., periodically, aperiodically) collects the vibration data (e.g., communicated from the sensors 220-228) corresponding to the component of the process control device 200.

At block 410, the received or collected vibration data is compared to a known threshold associated with the component of the process control device 200. In some examples, the vibration monitoring circuit 104 identifies the sensor from which the vibration data was received and the characteristic(s) of the vibration data (e.g., frequency, displacement, acceleration and/or velocity). The vibration monitoring circuit 104 compares the vibration data or characteristic(s) with the known threshold corresponding to the received vibration data. In some examples, the known threshold is retrieved from a local memory in the vibration monitoring circuit 104. In other examples, the vibration monitoring circuit 104 retrieves the known threshold from a remote storage. For example, the known threshold may be retrieved from the controller 106 or from a central facility via a data bus.

If the vibration data exceeds the known threshold, an alert message is sent (block 415). For example, the vibration monitoring circuit 104 and/or controller 106 generates and sends the alert message to the user interface 108, which displays the alert message via the output device 112. If the received vibration data does not exceed the known threshold, then the example method returns to block 405. Otherwise, the process ends.

In some examples, the vibration monitoring circuit 104 compares the vibration data or characteristic(s) of the vibration data with multiple thresholds. For example, vibration data exceeding a first threshold but less than a second threshold may indicate a loose mechanical connection (e.g., due to a broken piston ring on the valve plug 214) and vibration data exceeding the second threshold may indicate a damaged component (e.g., a broken actuator spring 234).

FIG. 5 is a flowchart representative of another example process or method 500 disclosed herein. The example process or method 500 begins by calculating a normalized vibration pattern associated with a process control device 200 component (block 505). For example, the vibration monitoring circuit 104 may process the vibration data and calculate a normalized vibration pattern based on the vibration data. This normalized vibration pattern represents an operating threshold or range (e.g., a natural frequency range) associated with the process control device 200 component during operation (e.g., during safe operation).

At block 510, the example vibration monitoring circuit 104 monitors vibration data subsequently collected from the sensor operatively coupled to the process control device 200 component (e.g., after calibration). In some examples, the vibration monitoring circuit 104 continuously (e.g., periodically, aperiodically, etc.) collects vibration data associated with the process control device 200.

At block 515, the example vibration monitoring circuit 104 or the example controller 106 determines whether the vibration data deviates from the normalized vibration pattern. For example, the vibration monitoring circuit 104 determines whether the vibration data falls outside of the operating range. If the vibration data falls outside of the operating range, an alert message is sent (block 520). If the vibration data is within the operating range, then the example method returns to block 510. Otherwise, the process ends.

In some examples, the vibration monitoring circuit 104 calibrates periodically (e.g., recalibrates). For example, the vibration monitoring circuit 104 calculates a normalized vibration pattern associated with the process control device 200 component every 24 hours. In some such examples, when the vibration data is within the operating range (e.g., no alert message was sent), the example method or process 500 includes a check to see whether recalibration should be initiated. For example, the vibration monitoring circuit 104 checks whether a timer has expired. If recalibration should be initiated, the example method returns to block 505 rather than block 510.

In other examples, the vibration monitoring circuit 104 recalibrates aperiodically. For example, the method or process 500 returns to block 505 when an alert message is sent.

FIG. 6 is a flowchart representative of another example process or method 600 disclosed herein. The example process or method 600 begins by collecting vibration data associated with a component of the process control device 200 and vibration data from a sensor operatively coupled to a pipe (e.g., the example upstream pipe 216 or the example downstream pipe 218 of FIG. 2), which is coupled to the process control device 200 (block 605). For example, the vibration monitoring circuit 104 collects vibration data from the actuator housing sensor 220 and the piping sensor 228. The example vibration monitoring circuit 104 calculates a transmissibility ratio based on the vibration data collected from the actuator housing sensor 220 and the piping sensor 228 (block 610). This transmissibility ratio compares the vibration data associated with the actuator (e.g., the displacement characteristic of the vibration data) relative to the vibration data associated with the pipe (e.g., the displacement characteristic of the vibration data).

At block 615, the example vibration monitoring circuit 104 or the controller 106 determines whether the transmissibility ratio exceeds a threshold. If the transmissibility ratio exceeds the threshold, an alert message is sent (block 620). If the transmissibility ratio does not exceed the threshold, then the example method returns to block 605. Otherwise, the process ends.

Figure 7:
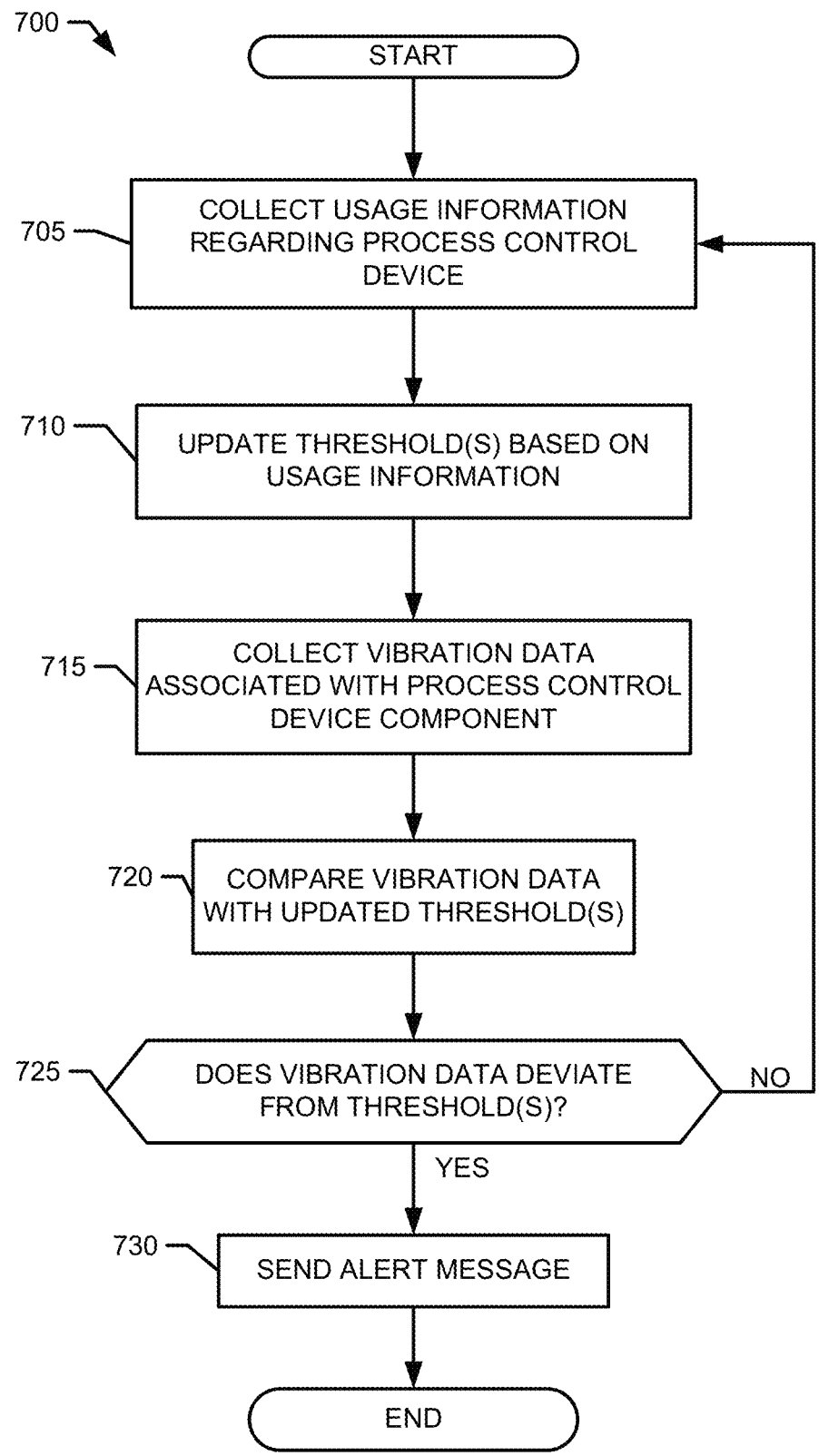
FIG. 7 is a flow chart representative of another example method disclosed herein.

FIG. 7 is a flowchart representative of another example process or method 700 disclosed herein. The example process or method 700 begins by collecting usage information regarding the process control device 200 (block 705). For example, the vibration monitoring circuit 104 communicates with a digital valve positioner (DVP) and receives information regarding, for example, operational cycles or distance traveled. The example vibration monitoring circuit 104 updates the threshold value(s) and/or range(s) based on the usage information (block 710). For example, during each operation cycle, the seal associated with the example valve plug 214 is subjected to a load and, thus, a stress. As a result, a portion of useful life is consumed. The example vibration monitoring circuit 104 adjusts (e.g., updates) the threshold value(s) and/or range(s) based on this reduced useful life information. The threshold value(s) and/or range(s) may be adjusted based on empirical or experimental data stored in a local memory in the example vibration monitoring circuit 104. Thus, the vibration monitoring circuit 104 adjusts the threshold value(s) and/or range(s) to reflect expected changes due to anticipated wear or damage through normal operation (e.g., distance traveled by the valve stem 210 during an operational cycle).

At block 715, the example vibration monitoring circuit 104 collects vibration data associated with a component of the process control device 200. At block 720, the collected vibration data is compared to the updated threshold value(s) and/or range(s) associated with the component of the process control device 200.

At block 725, the example vibration monitoring circuit 104 or the example controller 106 determines whether the vibration data exceeds the updated threshold value(s) and/or range(s). If the vibration data exceeds (or deviates from) the updated threshold(s), an alert message is sent (block 730). If the vibration data does not exceed (or deviate from) the updated threshold(s), then the example method returns to block 705. Otherwise, the process ends.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. An apparatus comprising:
    a vibration monitoring circuit configured to:
        collect, during calibration of a process control device, first vibration data from a first sensor coupled to the process control device;
        calculate an operating threshold of the process control device based on the first vibration data;
        collect usage information associated with the process control device, the usage information indicative of a remaining portion of useful life associated with the process control device;
        adjust the operating threshold based on the usage information, the adjusted operating threshold reflective of the remaining portion of useful life associated with the process control device;
        collect, after the calibration of the process control device, second vibration data from the first sensor;
        compare the second vibration data to the adjusted operating threshold;
        collect third vibration data from a second sensor coupled to a pipe, the pipe coupled to the process control device;
        calculate a ratio based on the second vibration data and the third vibration data;
        compare the ratio to a first threshold value;
        generate a first alert message in response to the second vibration data exceeding the adjusted operating threshold; and
        generate a second alert message in response to the ratio exceeding the first threshold value.

2. The apparatus of claim 1, wherein the first and second vibration data include acceleration data, velocity data, displacement data or frequency data.

3. The apparatus of claim 1, wherein the first threshold value depends on a coupling location of the first sensor.

4. The apparatus of claim 1, wherein the vibration monitoring circuit is further configured to:
    calculate a difference based on the third vibration data and the second vibration data;
    compare the difference to a second threshold value; and
    generate a third alert message in response to the difference exceeding the second threshold value.

5. The apparatus of claim 1, wherein the usage information includes operational cycles information or distance traveled.

6. An apparatus comprising:
    a vibration monitoring circuit configured to:
        collect first vibration data from a first sensor coupled to a process control device and second vibration data from a second sensor coupled to a pipe, the pipe coupled to the process control device;
        calculate a ratio based on the first vibration data and the second vibration data;
        collect usage information associated with the process control device, the usage information indicative of a remaining portion of useful life associated with the process control device;
        adjust a threshold value based on the usage information, the adjusted threshold value reflective of the remaining portion of useful life associated with the process control device;
        compare the ratio to the adjusted threshold value; and
        generate an alert message in response to the ratio exceeding the adjusted threshold value.

7. The apparatus of claim 6, wherein the first and second vibration data include acceleration data, velocity data, displacement data, or frequency data.

8. The apparatus of claim 6, wherein the threshold value depends on a coupling location of the first sensor.

9. An apparatus comprising:
    a vibration monitoring circuit configured to:
        collect first vibration data from a first sensor coupled to a process control device;
        access a predetermined diagnostic vibration pattern associated with the process control device;
        collect usage information associated with the process control device, the usage information indicative of a remaining portion of useful life associated with the process control device;
        adjust the predetermined diagnostic vibration pattern based on the usage information, the adjusted diagnostic vibration pattern reflective of the remaining portion of useful life associated with the process control device;
        compare the first vibration data to the adjusted diagnostic vibration pattern;
        collect second vibration data from a second sensor coupled to a pipe, the pipe coupled to the process control device;
        calculate a ratio between the first vibration data and the second vibration data;
        compare the ratio to a threshold value;
        generate a first alert message in response to the first vibration data deviating from the adjusted diagnostic vibration pattern; and
        generate a second alert message in response to the ratio exceeding the threshold value.

10. The apparatus of claim 9 wherein the first vibration data includes known vibration data ranges.

11. The apparatus of claim 9, wherein the first vibration data includes acceleration data, velocity data, displacement data or frequency data.

12. The apparatus of claim 9, wherein the threshold value depends on a coupling location of the first sensor.

13. The apparatus of claim 9, wherein the first vibration data includes a frequency range.

14. The apparatus of claim 13, wherein the frequency range indicates a control instability of the process control device.

15. The apparatus of claim 14, wherein the frequency range includes 1 Hertz to 10 Hertz.

16. The apparatus of claim 13, wherein the frequency range indicates a condition with a process flow associated with the process control device.

17. The apparatus of claim 16, wherein the frequency range includes 10 Hertz to 100 Hertz.

18. The apparatus of claim 13, wherein the frequency range indicates a condition associated with a valve trim of the process control device.

19. The apparatus of claim 18, wherein the frequency range includes frequencies greater than 100 Hertz.

20. An apparatus comprising:
a vibration monitoring circuit configured to:
collect usage information associated with a process control device, the usage information indicative of a remaining portion of useful life associated with the process control device;
adjust a known threshold range associated with the process control device based on the usage information, the adjusted known threshold range reflective of the remaining portion of useful life associated with the process control device;
collect first vibration data from a first sensor coupled to the process control device;
identify a characteristic of the process control device from the first vibration data;
compare the characteristic to the adjusted known threshold range;
collect second vibration data from a second sensor coupled to a pipe, the pipe coupled to the process control device;
calculate a ratio based on the first vibration data and the second vibration data;
compare the ratio to a threshold value;
generate a first alert message in response to the characteristic deviating from the adjusted known threshold range; and
generate a second alert message in response to the ratio exceeding the threshold value.

* * * * *

UNITED STATES PATENT AND TRADEMARK OFFICE
CERTIFICATE OF CORRECTION

PATENT NO. : 10,317,896 B2  
APPLICATION NO. : 15/354058  
DATED : June 11, 2019  
INVENTOR(S) : Anderson et al.

Page 1 of 1

It is certified that error appears in the above-identified patent and that said Letters Patent is hereby corrected as shown below:

On the Title Page

Item (71), Applicant, Line 2, replace "Mashalltown" with --Marshalltown--.

Item (72), Inventors, Lines 2 and 4, replace both instance of "Mashalltown" with --Marshalltown--.

Signed and Sealed this
Twentieth Day of August, 2019

Andrei Iancu
*Director of the United States Patent and Trademark Office*